(12) United States Patent
Hwang et al.

(10) Patent No.: US 10,945,708 B2
(45) Date of Patent: Mar. 16, 2021

(54) METHOD AND APPARATUS FOR REGISTRATION OF MEDICAL IMAGES

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Youngkyoo Hwang, Seoul (KR); Jungbae Kim, Seoul (KR); Youngtaek Oh, Seoul (KR); Wonchul Bang, Seongnam-si (KR); Jong Beom Ra, Daejeon (KR); Woo Hyun Nam, Seoul (KR); Chijun Weon, Busan (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 164 days.

(21) Appl. No.: 14/597,290

(22) Filed: Jan. 15, 2015

(65) Prior Publication Data
US 2015/0289848 A1    Oct. 15, 2015

(30) Foreign Application Priority Data
Apr. 14, 2014    (KR) ......................... 10-2014-0044423

(51) Int. Cl.
*A61B 8/08* (2006.01)
*A61B 5/055* (2006.01)
(Continued)

(52) U.S. Cl.
CPC ............ *A61B 8/5261* (2013.01); *A61B 5/055* (2013.01); *A61B 5/113* (2013.01); *A61B 5/1128* (2013.01);
(Continued)

(58) Field of Classification Search
CPC ..... A61B 8/5261; A61B 5/113; A61B 5/7289; A61B 5/1128; A61B 6/5288; A61B 6/486;
(Continued)

(56) References Cited

U.S. PATENT DOCUMENTS 8,369,597 B2 * 2/2013 Hyun ................. A61B 5/04284
382/131
2003/0233039 A1 12/2003 Shao et al.
(Continued)

FOREIGN PATENT DOCUMENTS

KR    10-2005-0063991 A    6/2005
KR    1020090127101 A    12/2009
(Continued)

OTHER PUBLICATIONS

Blackall et al. 2005 IEEE Trans. Med. Imaging 24:1403-1416.*
(Continued)

*Primary Examiner* — Keith M Raymond
*Assistant Examiner* — Patrick M Mehl
(74) *Attorney, Agent, or Firm* — Sughrue Mion, PLLC

(57) ABSTRACT

A medical image registration method and apparatus are described. By performance of a medical image registration method, a highly accurate registered image, in which breathing deformation information is considered, may be obtained by generation of non-real-time medical images in which the breathing deformation information is reflected before a medical procedure is conducted and by rigid registration of a real-time medical image and the generated non-real-time medical images during the medical procedure.

12 Claims, 8 Drawing Sheets

(51) Int. Cl.
*A61B 6/03* (2006.01)
*A61B 8/00* (2006.01)
*A61B 6/00* (2006.01)
*A61B 5/11* (2006.01)
*A61B 5/113* (2006.01)
*A61B 5/00* (2006.01)
*G06T 7/33* (2017.01)
*G01R 33/56* (2006.01)

(52) U.S. Cl.
CPC ............ *A61B 5/7289* (2013.01); *A61B 6/032* (2013.01); *A61B 6/4417* (2013.01); *A61B 6/486* (2013.01); *A61B 6/5247* (2013.01); *A61B 6/5288* (2013.01); *A61B 8/463* (2013.01); *G06T 7/33* (2017.01); *A61B 6/037* (2013.01); *A61B 2505/05* (2013.01); *A61B 2576/02* (2013.01); *G01R 33/5608* (2013.01); *G06T 2207/10072* (2013.01); *G06T 2207/10116* (2013.01); *G06T 2207/10132* (2013.01)

(58) Field of Classification Search
CPC ..... A61B 6/5247; A61B 6/4417; A61B 5/055; A61B 8/463; A61B 6/032; A61B 2576/02; A61B 2576/00; A61B 2505/05; A61B 6/037; G06T 7/0028; G06T 2207/10132; G06T 7/33; G06T 2207/10072; G06T 2207/10116; G01R 33/5608; G16H 30/40
See application file for complete search history.

(56) References Cited

U.S. PATENT DOCUMENTS

| | | |
|---|---|---|
| 2011/0028843 A1 | 2/2011 | Hyun et al. |
| 2012/0230556 A1 | 9/2012 | Wollenwebber |
| 2013/0063434 A1 | 3/2013 | Miga et al. |
| 2013/0261429 A1* | 10/2013 | Lee ................... A61B 5/0035 600/411 |
| 2013/0345545 A1* | 12/2013 | Gross .................. A61B 5/055 600/411 |
| 2014/0037161 A1* | 2/2014 | Rucker .................. G06T 7/30 382/128 |
| 2014/0153806 A1* | 6/2014 | Glielmi ................ G01R 33/481 382/131 |

FOREIGN PATENT DOCUMENTS

| | | |
|---|---|---|
| KR | 10-2011-0013026 A | 2/2011 |
| KR | 101080605 B1 | 11/2011 |

OTHER PUBLICATIONS

King et al. 2010 IEEE Trans. Med. Imaging 29:924-937.*
Lee et al. 2011 Phys. Med. Biol. 56:117-137.*
Schreibmann et al. 2006 Int.J.Rad. Oncol. Biol. Phys. 64:1537-1550.*
Roche et al. 2001 IEEE Trans. Med. Imaging 20:1038-1049.*
Melbourne et al. 2012 Proc. SPIE 8314 Medical Imaging 2012: Image Processing, 83141Z-1-83141Z-10.*
Jenkinson et al. 2002 NeuroImage 17:825-841.*
Huang et al. 2009 IEEE Transactions on Medical Imaging 28:1802-1814; Pub.Date Oct. 28, 2009 (Year: 2009).*
Lee et al. 2010 IEEE International Symposium on Biomedical Imaging pp. 388-391 (Year: 2010).*
Norweck et al. 2013 J. Digit. Imaging 26:38-52 ePub Sep. 20, 2012 (Year: 2012).*
Communication dated Jul. 7, 2020, issued by the Korean Intellectual Property Office in corresponding Korean Application No. 10-2014-0044423

* cited by examiner

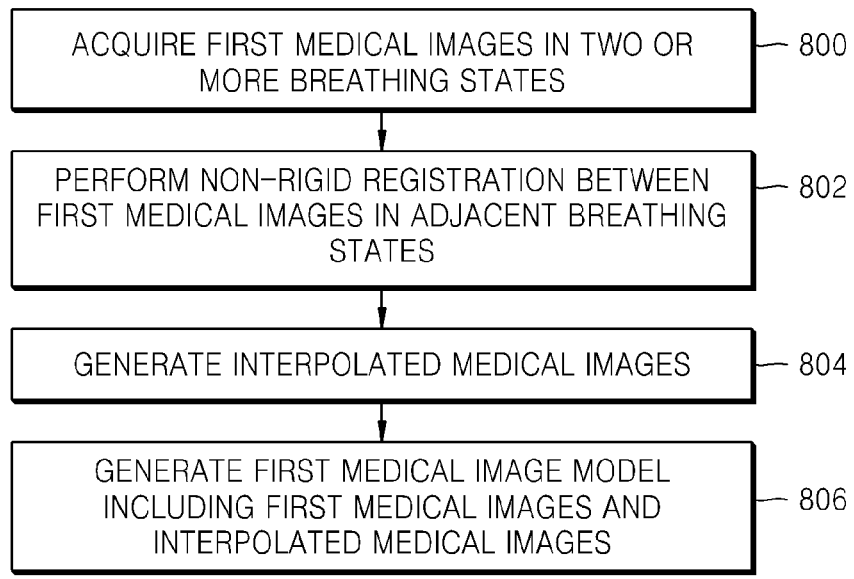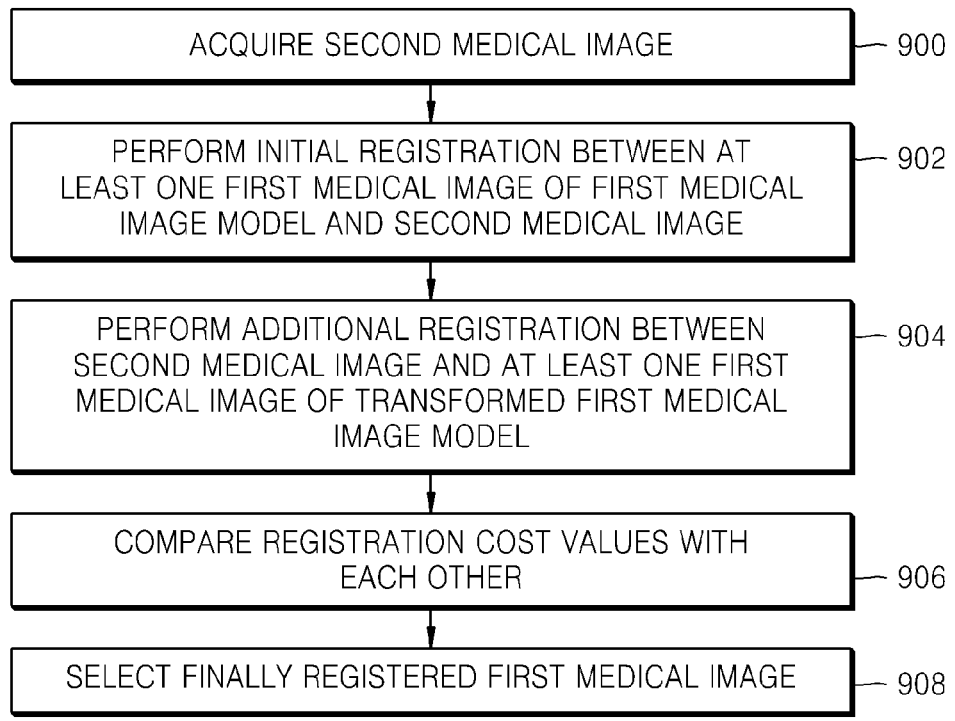

METHOD AND APPARATUS FOR REGISTRATION OF MEDICAL IMAGES

CROSS-REFERENCE TO RELATED APPLICATION

This application claims priority from Korean Patent Application No. 10-2014-0044423, filed on Apr. 14, 2014, in the Korean Intellectual Property Office, the disclosure of which is incorporated herein by reference in its entirety.

BACKGROUND

1. Field

Exemplary embodiments relate to methods and apparatuses for registration of medical images by considering physical activities of a subject.

2. Description of the Related Art

Recently, with the ability to obtain high resolution medical images and the possibility of performing minimally invasive surgery (MIS) using medical equipment, as well as developments in medical technology, a method for treating the human body while observing the inside of the human body with a medical imaging device by making a small hole in the skin and directly inserting a catheter or a medical needle into a blood vessel of a desired part of the human body without a direct incision into the human body has been developed. This is called "a procedure using images" or "an interventional imaging procedure". A medical practitioner perceives a location of an organ or a lesion through an image. Furthermore, a patient breathes or moves during a procedure, and accordingly, the medical practitioner needs to take into consideration a change according to the breathing or movement of the patient. Thus, the medical practitioner is supposed to perform the procedure by accurately and quickly perceiving the breathing or movement of the patient based on real-time images, and in this case, it is not easy to perceive a shape of the organ or the lesion on the real-time images with the naked eye. Compared with ultrasound images, organs and lesions may be clearly identified from magnetic resonance (MR) or computed tomography (CT) images. However, since the MR or CT images cannot be acquired in real-time during a medical procedure, the breathing and movement of a patient, which occur during the medical procedure, are not reflected therein.

SUMMARY

Provided are medical image registration methods and apparatuses capable of outputting a highly accurate registered image, in which breathing deformation information is considered, by generation of non-real-time medical images in which the breathing deformation information is reflected before a medical procedure and by rigid registration of a real-time medical image and the generated non-real-time medical images during the medical procedure.

Additional aspects will be set forth in part in the description which follows and, in part, will be apparent from the description, or may be learned by practice of the presented exemplary embodiments.

According to an aspect of one or more exemplary embodiments, a medical image registration method includes: generating a first medical image model based on first medical images captured during at least two breathing states of a subject; acquiring a second medical image of a region of interest (ROI) of the subject; performing an initial registration between at least a first one of the first medical images which is selected from the generated first medical image model and the acquired second medical image; transforming the generated first medical image model by using a registration parameter which is determined based on the initial registration; performing a second registration between at least a second one of the first medical images which is selected from the transformed first medical image model and the acquired second medical image; and outputting a combined image which is based on a result of the second registration.

The first medical image model may include the first medical images and an interpolated medical image of an intermediate breathing state that is adjacent to the at least two breathing states, the interpolated medical image being generated by interpolating at least two of the first medical images.

The first medical image model may include a set of four-dimensional (4D) medical images, which includes a plurality of 3D first medical images which are generated based on the first medical images and an interpolated 3D medical image of an intermediate breathing state that is adjacent to the at least two breathing states, the interpolated 3D medical image being interpolated by using a displacement vector which is determined as a result of a non-rigid registration with respect to the plurality of 3D medical images.

The interpolated 3D medical image may be interpolated by performing a linear segmentation or a nonlinear segmentation of the displacement vector with respect to the plurality of 3D medical images.

The initial registration may be performed by matching respective landmark points extracted from the selected at least first one of the first medical images with corresponding landmark points extracted from the second medical image.

The registration parameter may be determined by matching respective landmark points of a first medical image captured during an inhalation state from among the at least two breathing states with the corresponding landmark points of the second medical image, and the transforming may include transforming the first medical images included in the first medical image model by using the determined registration parameter.

At least three registration parameters may be determined by matching respective landmark points of each of at least three from among the first medical images which respectively correspond to an inhalation state, a half inhalation/ exhalation state, and an exhalation state from among the at least two breathing states with the corresponding landmark points of the second medical image, and an interpolated registration parameter may be interpolated using the determined at least three registration parameters, and the transforming may include using the determined at least three registration parameters and the interpolated registration parameter.

A plurality of registration parameters may be determined by matching respective landmark points of all of the first medical images with the corresponding landmark points of the second medical image, and the transforming may include using all of the plurality of registration parameters.

The second registration may be performed based on an intensity and a gradient of the selected at least first one of the first medical images with respect to the second medical image.

The method may further include down-sampling the selected at least first one of the first medical images, performing the second registration between the down-sampled medical image and the second medical image, up-sampling at least a second one of the first medical images, and performing at least a third registration between the up-sampled medical images and the second medical image.

The second registration may be performed for at least three of the first medical images which correspond to an inhalation state, a half inhalation/exhalation state, and an exhalation state from among the at least two breathing states from the transformed first medical image model and the second medical image, and a third registration may be performed for a fourth one of the first medical images and the second medical image.

After performing the second registration, the first medical image model may be updated by segmenting the displacement vector based on a selected one of the first medical images and interpolating the selected one of the first medical images.

Each of the first medical images may include one from among a magnetic resonance (MR) image, a computed tomography (CT) image, a positron emission tomography (PET) image, and an X-ray image captured before a medical procedure is conducted, and the second medical image may include one from among a 3D ultrasound image and a 2D ultrasound image captured during the medical procedure.

According to another aspect of one or more exemplary embodiments, a medical image registration apparatus includes: a medical image model generator configured to generate a first medical image model based on first medical images captured during at least two breathing states of a subject; a medical image acquisition module configured to acquire a second medical image of a region of interest (ROI) of the subject; an initial registration module configured to perform an initial registration between at least a first one of the first medical images which is selected from the generated first medical image model and the acquired second medical image; an additional registration module configured to perform at least a second registration between at least a second one of the first medical images which is selected from a transformed first medical image model and the acquired second medical image; and a controller configured to transform the first medical image model by using a registration parameter which is determined based on the initial registration and to provide the transformed first medical image model to the additional registration module and to output a combined image which is based on a result of the second registration.

The first medical image model may include the first medical images and an interpolated medical image of an intermediate breathing state that is adjacent to the at least two breathing states, the interpolated medical image being generated by interpolating at least two of the first medical images.

The medical image model generator may be further configured to generate a set of four-dimensional (4D) medical images, which includes a plurality of 3D medical images which are generated based on the first medical images and an interpolated 3D medical image of an intermediate breathing state that is adjacent to the at least two breathing states, the interpolated 3D medical image being interpolated by using a displacement vector which is determined as a result of a non-rigid registration with respect to the plurality of 3D medical images.

The medical image model generator may be further configured to interpolate the interpolated 3D medical image by performing a linear segmentation or a nonlinear segmentation of the displacement vector with respect to the plurality of 3D medical images.

The initial registration module may be further configured to match respective landmark points extracted from the selected at least first one of the first medical images with corresponding landmark points extracted from the second medical image.

The additional registration module may be further configured to perform the at least second registration based on an intensity and a gradient of the selected at least first one of the first medical images and the second medical image.

Each of the first medical images may include one from among a magnetic resonance (MR) image, a computed tomography (CT) image, a positron emission tomography (PET) image, and an X-ray image captured before a medical procedure is conducted, and the second medical image may include one from among a 3D ultrasound image and a 2D ultrasound image captured during the medical procedure.

BRIEF DESCRIPTION OF THE DRAWINGS

These and/or other aspects will become apparent and more readily appreciated from the following description of exemplary embodiments, taken in conjunction with the accompanying drawings in which:

FIG. 8 is a flowchart of a method for generating a non-real-time medical image model before a medical procedure is conducted;

FIG. 9 is a flowchart of a medical image registration method performed during a medical procedure.

DETAILED DESCRIPTION

Figure 1:
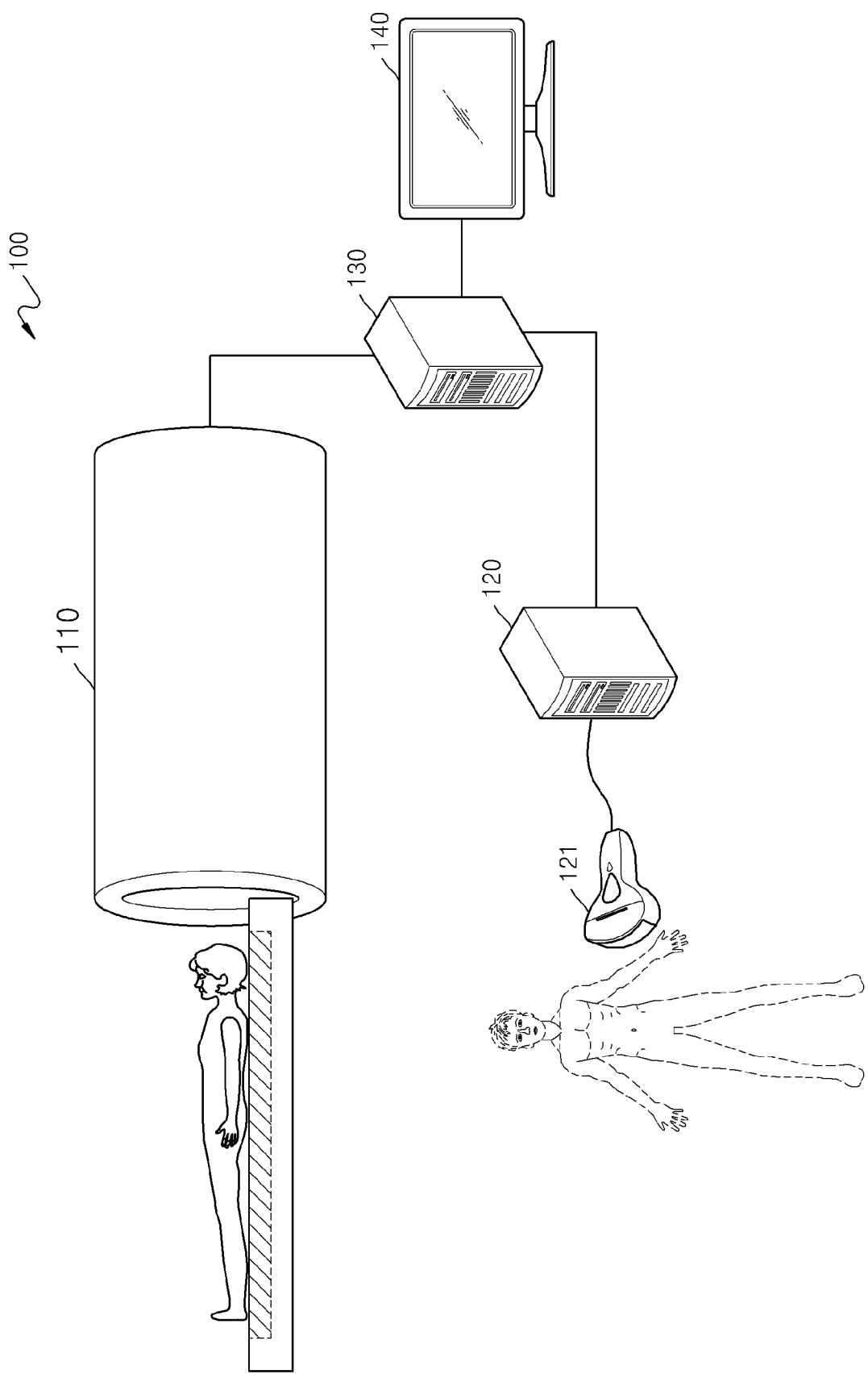
FIG. 1 is a conceptual diagram of a medical imaging system, according to an exemplary embodiment.

The exemplary embodiments may allow various kinds of change or modification and various changes in form, and specific embodiments will be illustrated in drawings and described in detail in the specification. However, it should be understood that the specific embodiments do not limit the inventive concept to a specific disclosed form but include every modified, equivalent, or replaced one within the disclosed spirit and technical scope. In the following description, well-known functions or constructions are not described in detail so as not to obscure the present disclosure with unnecessary detail.

Although terms, such as 'first' and 'second', can be used to describe various elements, the elements cannot be limited by the terms. The terms can be used to classify a certain element from another element.

The terminology used in the application is used only to describe specific exemplary embodiments and does not have any intention to limit the scope of rights. An expression in the singular includes an expression in the plural unless they are clearly different from each other in context. In the application, it should be understood that terms, such as 'include' and 'have', are used to indicate the existence of an implemented feature, number, step, operation, element, part, or a combination thereof without excluding in advance the possibility of the existence or addition of one or more other features, numbers, steps, operations, elements, parts, or combinations thereof.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

FIG. 1 is a conceptual diagram of a medical imaging system 100, according to an exemplary embodiment. Referring to FIG. 1, the medical imaging system 100 includes a first medical device 110, a second medical device 120, a medical image registration apparatus 130, and an image display device 140.

The first medical device 110 generates a first medical image for a volume of interest (VOI) of a subject before a medical procedure is conducted. For example, the first medical device 110 may include any one of a computed tomography (CT) imaging device, a magnetic resonance (MR) imaging device, an X-ray imaging device, and a positron emission tomography (PET) imaging device. Hereinafter, it is assumed for convenience of description that the first medical image is an MR image or a CT image. A location of an organ or lesion may be clearly identified from the CT image or from the MR image generated by the first medical device 110. However, according to the CT or MR image, an image in which a real-time change in a shape or location of an organ is reflected when a patient breathes or turns over during a medical procedure cannot be acquired. Because the image cannot be output in real-time, it is recommended to capture CT images for a short time because of the concern of over-exposure of a patient and a medical practitioner to radioactivity when a capturing method uses radiation, and thus, it takes a relatively long time to capture MR images. In general, CT images are captured when a patient temporarily stops breathing, e.g., in a maximum inhalation state.

In one or more exemplary embodiments, two or more MR/CT images (i.e., first medical images) are acquired by the first medical device 110. The two or more first medical images may correspond to different breathing states. For example, the two or more first medical images may include a large amount of breathing deformation information of a patient when the breathing states differ greatly from each other, such as, for example, a maximum inhalation state and a maximum exhalation state. In addition, when it is possible to acquire a larger number of first medical images, a medical image model which approximates actual breathing deformation information of the patient may be generated when a higher number of images are acquired in a half inhalation/exhalation state. In addition, when two or more organs in one region of interest (ROI) are supposed to be photographed in an intra-operative stage, since deformation patterns of the two or more organs in an actual breathing period may differ from each other, medical images which approximate an actual breathing pattern may be acquired through half inhalation/exhalation capturing. Therefore, deformation information on a motion and shape of each organ which varies according to breathing of the subject may be reflected. The first medical device 110 provides first medical images captured in two or more breathing states, which are acquired in a pre-operative stage, to the medical image registration apparatus 130, and the medical image registration apparatus 130 generates a first medical image model based on the first medical images. The first medical image model will be described below.

The second medical device 120 provides medical images for the VOI of the subject in real-time. Thus, a change in the medical images according to the physical activity of the subject may be observed using the second medical device 120. According to an exemplary embodiment, the second medical device 120 may include an ultrasonography machine which is configured for generating real-time images during an interventional medical procedure for a patient. The second medical device 120 irradiates ultrasound signals toward an ROI by using a probe 121 equipped in the second medical device 120 and generates an ultrasound image by detecting reflected ultrasound signals. The probe 121 usually includes a piezoelectric transducer but is not limited thereto. When ultrasound waves from within a range of approximately several MHz to hundreds of MHz are delivered to a predetermined part inside the human body of a patient from the probe 121, the ultrasound waves are partially reflected from layers between different tissues. In particular, the ultrasound waves are reflected from parts inside the human body that vary in density, e.g., blood cells in blood plasma, small structures in organs, and the like. The reflected ultrasound waves make the piezoelectric transducer of the probe 121 vibrate, and the piezoelectric transducer outputs electrical pulses in response to the vibration. These electrical pulses are transformed into an image.

As described above, medical images acquirable by the second medical device 120, e.g., ultrasound images, may be obtained in real-time, but since the ultrasound images include a significant amount of noise, it may be difficult to identify an outline of an organ, an internal structure, and/or a lesion from the ultrasound images, because contrast of brightness and darkness at an interface between a lesion and surrounding tissue, i.e., edge contrast of an object, may be relatively low in the ultrasound images since the lesion and the surrounding tissue have similar ultrasound characteristics. In addition, noise and artifacts due to interference and dispersion of ultrasound waves exist in the ultrasound images. In particular, while ultrasound medical images may be acquired more quickly than MR or CT images, the ultrasound medical images have a relatively low signal-to-noise ratio (SNR) and relatively low edge contrast with respect to an object, and thus, an organ and a lesion, which are identifiable in the MR or CT images, may not be clearly identified from surrounding tissue in the ultrasound medical images.

The medical images captured by the first medical device 110 and the second medical device 120 may be three-dimensional (3D) medical images generated by accumulating cross-sectional images, which are two-dimensionally captured. For example, the first medical device 110 captures a plurality of cross-sectional images while changing locations and orientations of the cross-sectional images. When the cross-sectional images are accumulated, 3D volume image data which three-dimensionally represents a predetermined part of the human body of a patient may be generated. This method of generating 3D volume image data by accumulating cross-sectional images is called a multi-planar reconstruction (MPR) method. Hereinafter, it is assumed that all images captured by the first medical device 110 and the second medical device 120 are three-dimensional.

The second medical device 120 acquires a second medical image from a region to be checked and/or an ROI in an intra-operative stage, and provides the second medical image to the medical image registration apparatus 130.

The medical image registration apparatus 130 generates a first medical image model based on first medical images captured by the first medical device 110 in two or more breathing states of the subject and acquires a second medical image of an ROI of the subject. The first medical image model may include a set of first medical images acquired before a medical procedure is conducted, and the second medical image may be a medical image acquired during the medical procedure. For example, the first medical images may include CT/MR images, and the second medical image may be an ultrasound image. The medical image registration apparatus 130 may select a first medical image that is most similar to the second medical image acquired during the medical procedure through registration between at least one first medical image selected from the first medical image model and the acquired second medical image.

Figure 2:
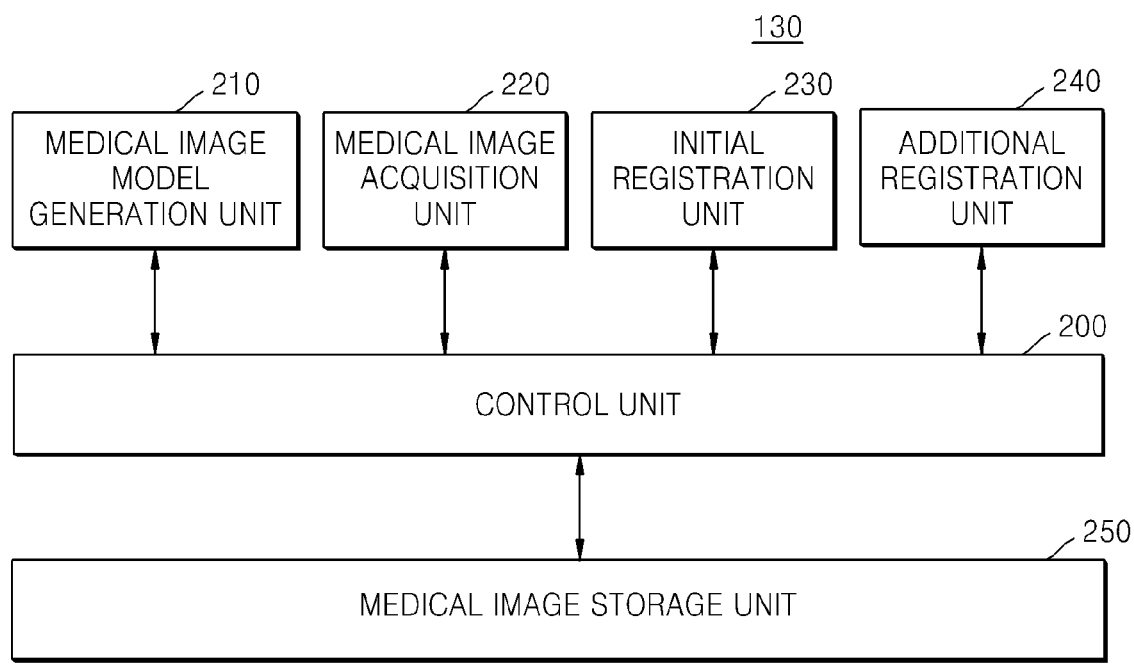
FIG. 2 is a block diagram of a medical image registration apparatus in the medical imaging system of FIG. 1.

Referring to FIG. 2, the medical image registration apparatus 130 includes a control unit (also referred to herein as a "controller") 200, a medical image model generation unit (also referred to herein as a "medical image model generator") 210, a medical image acquisition unit (also referred to herein as a "medical image acquisition device" and/or as a "medical image acquisition module") 220, an initial registration unit (also referred to herein as an "initial registration device" and/or as an "initial registration module") 230, an additional registration unit (also referred to herein as an "additional registration device" and/or as an "additional registration module") 240, and a medical image storage unit (also referred to herein as a "medical image storage device" and/or as a "medical image storage") 250.

The medical image model generation unit 210 generates a first medical image model on the basis of first medical images captured in two or more breathing states. The first medical image model may be a set of first medical images, which includes the first medical images and an interpolated medical image of an intermediate breathing state that is adjacent to the two or more breathing states, the interpolated medical image being generated by interpolating the first medical images. When the first medical images are 3D medical images, the first medical image model may be a set of 4D medical images, which includes an interpolated 3D first medical image of an intermediate breathing state that is adjacent to the two or more breathing states, the 3D first medical image being interpolated using a displacement vector which is determined by performing a non-rigid registration with respect to the 3D first medical images. Here, "non-rigid registration" refers to a registration method in which a shape of an object is deformed.

Figure 3:
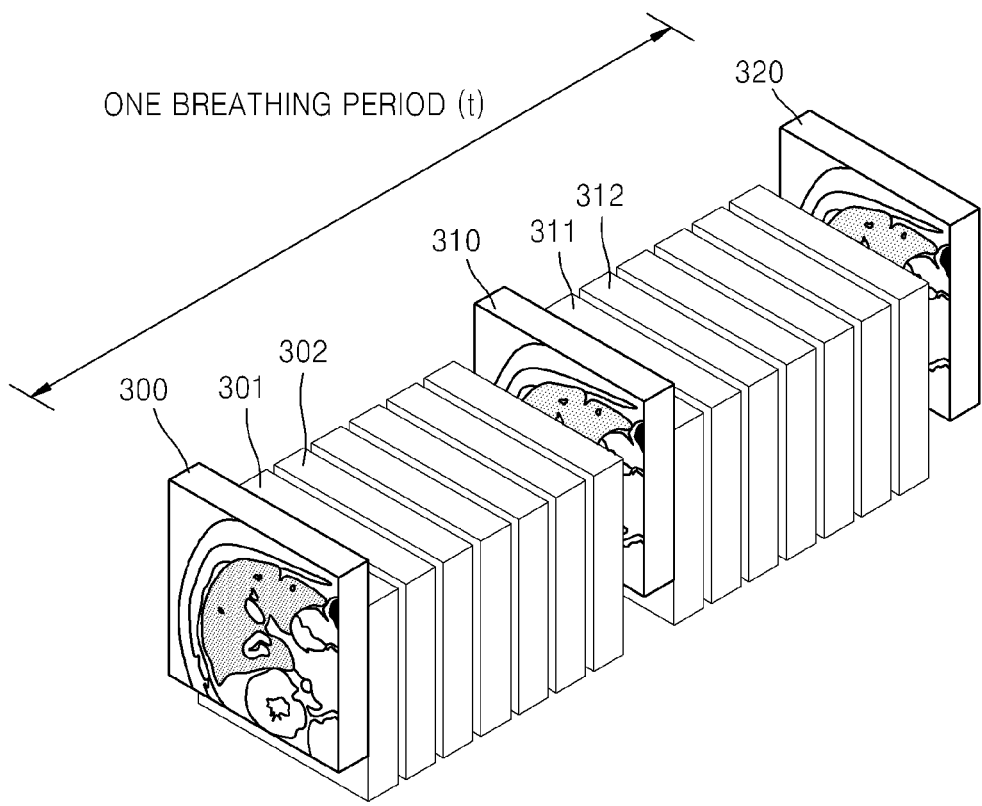
FIG. 3 illustrates a non-real-time medical image model.

Referring to FIG. 3, a first medical image model is illustrated. The first medical image model is a set of 3D first medical images 300 to 320, and includes three first medical images 300, 310, and 320 acquired by the first medical device 110 and first medical images 301, 302, 311, and 312 interpolated using the three first medical images 300, 310, and 320. The three first medical images 300, 310, and 320 are medical images which are captured in a maximum inhalation state, a half inhalation/exhalation state, and a maximum exhalation state, respectively, the first medical images 301 and 302 are medical images interpolated using the first medical image 300 captured in the maximum inhalation state and the first medical image 310 captured in the half inhalation/exhalation state, and the first medical images 311 and 312 are medical images interpolated using the first medical image 310 captured in the half inhalation/exhalation state and the first medical image 320 captured in the maximum exhalation state. The interpolation of medical images is performed such that the interpolated first medical image 301 is generated by performing non-rigid registration on medical images in adjacent breathing states, e.g., the medical image 300 captured in the maximum inhalation state and the first medical image 310 captured in the half inhalation/exhalation state, and using a displacement vector determined by performing the non-rigid registration. Therefore, a 4D first medical image model may be generated by generating a first medical image model that is a set of first medical images for one breathing period t, wherein the one breathing period t indicates an average time length of one period in periodical breathing of the subject repeating inhalation and exhalation. However, according to exemplary embodiments, first medical images may be captured for a time length of more than the one period. In addition, since the first medical image model shown in FIG. 3 is generated in advance with respect to first medical images acquired by the first medical device 110 before a medical procedure is conducted, non-rigid registration in which a shape of an object is deformed may be used, and thus, image registration may be more accurate than rigid registration. Although first medical images captured in three breathing states, i.e., a maximum inhalation state, a half inhalation/exhalation state, and a maximum exhalation state, have been described with reference to FIG. 3, one or more exemplary embodiments are not limited thereto, and the first medical images may be captured in two breathing states or other breathing states.

For example, two or more 3D MR/CT images are acquired to generate a 4D MR/CT image including information on deformation in terms of motion and shape of each organ changing in correspondence with breathing in a pre-operative stage, wherein two of the two or more 3D MR/CT images are captured in different breathing states. Much breathing deformation information of a patient may be acquired as the two breathing states may differ greatly from each other, such as, for example, maximum exhalation/maximum inhalation, and when three or more 3D MR/CT images are captured, a 4D MR/CT image closer to actual breathing deformation information of the patient may be generated as a higher number of images are acquired in half inhalation/exhalation. Particularly, when two or more organs in one ROI are supposed to be captured in an intra-operative stage, since deformation patterns of the two or more organs may differ in an actual breathing period, a 4D MR/CT image relatively close to an actual breathing pattern may be generated through half inhalation/exhalation capturing. After acquiring the 3D MR/CT images, non-rigid registration between images in adjacent breathing states is performed. A displacement vector which is determined by performing the non-rigid registration is used to interpolate an intermediate image between breathing states. For two 3D MR/CT images, interpolation images between the two images may be generated by linearly segmenting a displacement vector. When two or more actual images of a half inhalation/exhalation state are acquired, interpolation images may be generated by nonlinearly segmenting a displacement vector by cardinal-spline interpolation not so as to generate sharply deformed interpolation images. The cardinal-spline interpolation may control a sudden change in linear interpolation. Therefore, by generating a 4D MR/CT image including deformation information of an organ according to breathing through non-rigid registration, in an intra-operative stage, a highly-accurate registration result having deformation information may be obtained even only with rigid registration.

The medical image acquisition unit 220 acquires a plurality of first medical images of a subject, which are captured by the first medical device 110 for a preset time. The medical image acquisition unit 220 acquires the first medical images and provides the acquired first medical images to the medical image model generation unit 210 before a medical procedure is conducted, and the medical image model generation unit 210 generates a first medical image model as shown in FIG. 3. The medical image acquisition unit 220 includes interfaces for acquiring medical images from the first medical device 110 and the second medical device 120. The medical image acquisition unit 220 acquires medical images captured by the first medical device 110 and the second medical device 120 under control of the control unit 200.

The initial registration unit 230 selects at least one first medical image from the first medical image model generated by the medical image model generation unit 210, and performs initial registration between the selected at least one first medical image and the second medical image acquired by the second medical device 120. The initial registration may be a rigid registration which is based on landmark points, and since the first medical image and the second medical image are captured by different medical devices (first and second medical devices 110 and 120), the initial registration may be a heterogeneous image registration. The initial registration unit 230 may minimize an error in the heterogeneous image registration, and quickly and accurately perform the heterogeneous image registration by performing registration between images, partial images or all images, captured in same or most similar breathing states.

The initial registration unit 230 performs the initial registration via landmark point matching by extracting corresponding landmark points from the first medical image and the second medical image. The number of extracted landmark points may be two or more, and is not limited to any particular number.

A landmark point indicates a point used as a reference in image registration and may be extracted from anatomical objects shown in the first medical image and the second medical image. The anatomical objects include components of the subject, such as organs, blood vessels, lesions, bones, inter-organ interfaces, and the like, but are not limited thereto.

Landmark points may be extracted using any one or more of the following methods:

A. A point at which an anatomical feature of an object is distinctively reflected is defined as a landmark point. For example, when an object from which landmark points are extracted is the liver, points at which blood vessels diverge in a blood vessel structure inside the liver may be extracted as landmark points, and when an object from which landmark points are extracted is the heart, an interface at which the right atrium and the left atrium divide and an interface at which the main vein and the outer wall of the heart meets may be extracted as landmark points.

B. The highest or lowest point of an object from which landmark points are extracted in a pre-defined coordinate system may also be designated as a landmark point.

C. Points for interpolating between the landmark points selected in A and B may be selected with a constant gap along the object and designated as landmark points.

When the designated landmark points are two-dimensional, the designated landmark points may be represented with coordinates of the x-axis and the y-axis, and when the designated landmark points are three-dimensional, the designated landmark points may be represented with coordinates of the x-axis, the y-axis, and the z-axis. Thus, when coordinates of three-dimensional landmark points are represented as vectors $x_0, x_1, \ldots, x_{n-1}$ (n denotes the number of landmark points), the coordinates of the three-dimensional landmark points may be represented by Equation 1 below:

$$x_{i0} = [x_{i0}, y_{i0}, z_{i0}] \quad (1)$$
$$x_{i1} = [x_{i1}, y_{i1}, z_{i1}]$$
$$\vdots$$
$$x_{in-1} = [x_{in-1}, y_{in-1}, z_{in-1}]$$

In Equation 1, i denotes landmark point coordinate information in an $i^{th}$ first medical image.

A transform function for rotating, scaling, translating, or shearing any one of the first medical image and the second medical image based on the other one thereof is calculated by using the extracted landmark points. The transform function may be an affine transform function $T_{affine}$ calculated by using an affine registration scheme. For example, the affine transform function $T_{affine}$ may be calculated by using an iterative closest point (ICP) algorithm. The ICP algorithm is an algorithm for minimizing a distance difference between corresponding landmark points from among cases where landmark points in different images are in one-to-one correspondence.

Figure 10:
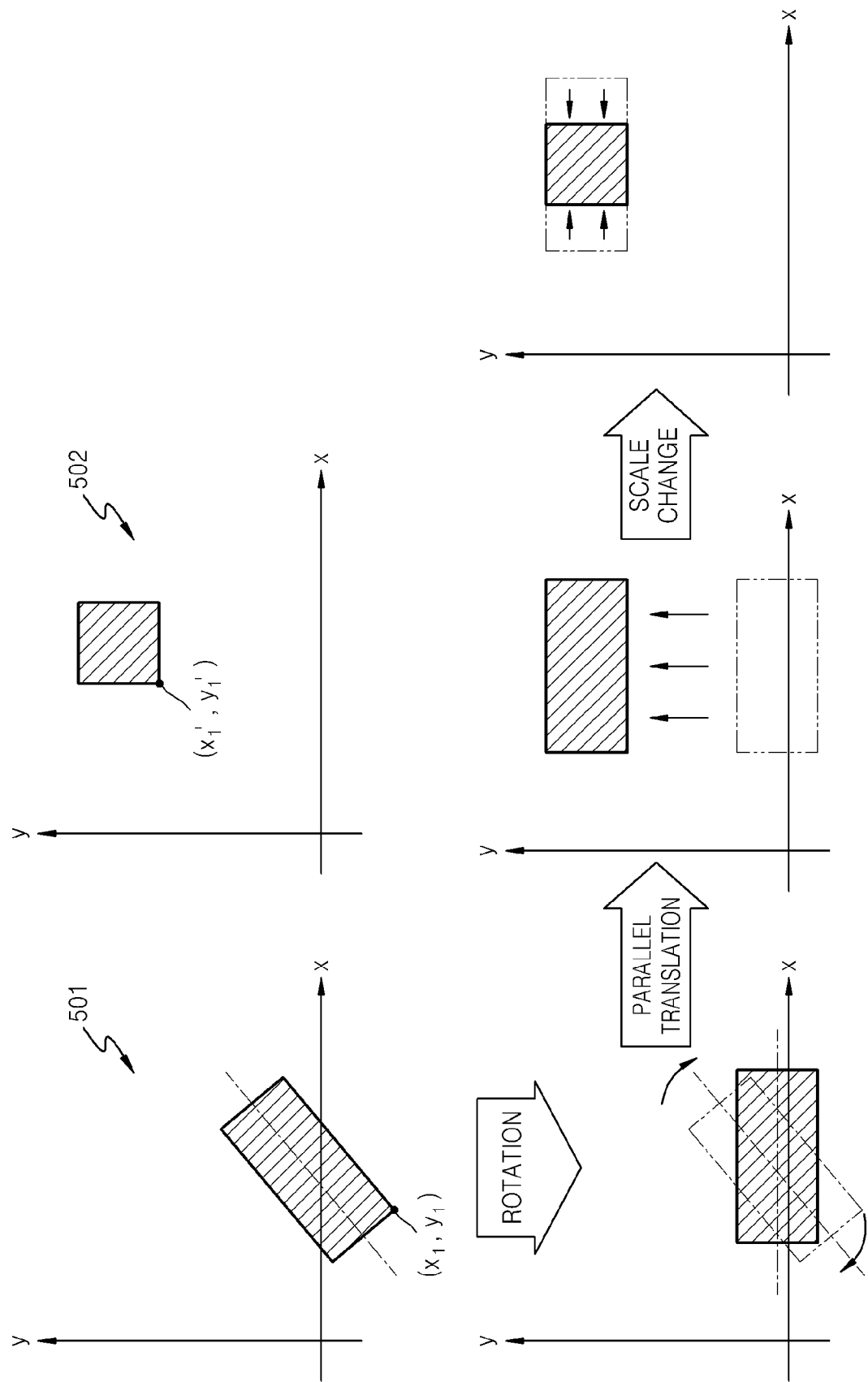
FIG. 10 illustrates a method for acquiring an affine transform function Taffine from a two-dimensional image.

FIG. 10 illustrates a method for acquiring the affine transform function $T_{affine}$ from a 2D image. Reference numeral 501 denotes a state before the affine transform function $T_{affine}$ is applied, and reference numeral 502 denotes a state to be transformed by applying the affine transform function $T_{affine}$. Since an affine transform involves one-to-one point correspondence, the affine transform function $T_{affine}$ may be determined by Equation 2 below:

$$\begin{bmatrix} x'_1 \\ y'_1 \end{bmatrix} = T_{affine} \begin{bmatrix} x_1 \\ y_1 \\ 1 \end{bmatrix} = \begin{bmatrix} a_1 & b_1 & c_1 \\ a_2 & b_2 & c_2 \end{bmatrix} \begin{bmatrix} x_1 \\ y_1 \\ 1 \end{bmatrix} \quad (2)$$

Coordinates of the first medical image or the second medical image may be transformed or inverse transformed by using the transform function described above. When it is assumed that a first point in the first medical image corresponds to a second point in the second medical image, the first point may be transformed or inverse transformed to the second point by coordinate transformation.

In the initial registration, the at least one first medical image to be matched with the second medical image may be selected from the first medical image model shown in FIG. 3 by applying any one or more of the following methods.

One method includes performing the initial registration with one first medical image. One first medical image which is determined to relate to a breathing state similar to that of the acquired second medical image is selected from the first medical image model, and the initial registration is performed between the selected first medical image and the second medical image. For example, when the second medical image is captured in a maximum exhalation state during a medical procedure, a first medical image of an exhalation state is selected. This selection may be usually used when the accuracy of a parameter in the initial registration is high by predicting a similar parameter for other breathing states. Although it has been mainly described that medical images are determined to have a similar breathing state, one or more exemplary embodiments are not limited thereto, and a first medical image for the initial registration may be selected by applying any of various methods for determining similarity between each of first medical images and the second medical image. For example, a Gabor wavelet scheme or a local binary pattern matching scheme may be used to determine the similarity, but is not limited thereto.

Another method includes performing the initial registration with three or four first medical images. For example, the initial registration is performed between one ultrasound image and each of three or four first medical images selected with respect to a near inhalation state, a half inhalation/exhalation state, and an exhalation state. Thereafter, an initial registration parameter for the other first medical images is generated by approximating parameters which are determinable as a result of the initial registration by a simple parameter interpolation method.

Another method includes performing the initial registration with all of the first medical images included in the first medical image model. The initial registration is performed between each of the first medical images and the second medical image. This method may be used when the initial registration has a somewhat low accuracy but is sufficiently fast.

The control unit 200 transforms the first medical image model by using the registration parameter which is determined based on the initial registration performed by the initial registration unit 230, wherein the registration parameter may be a coordinate transform parameter which relates to a transform function between the first medical image and the second medical image.

The additional registration unit 240 performs additional registration(s) between at least one first medical image selected from the transformed first medical image model and the second medical image. The additional registration(s) may include a registration to which an optimization scheme is applied, and may include a rigid registration which is based on an intensity and a gradient of an image. Since registration between images is not dependent on each other in the additional registration(s), the additional registration(s) may be processed in parallel by using a graphic processing unit (GPU) for each registration. Like the initial registration, some exemplary embodiments which relate to the additional registration(s) will be described below with reference to FIGS. 5, 6, and 7.

Figure 5:
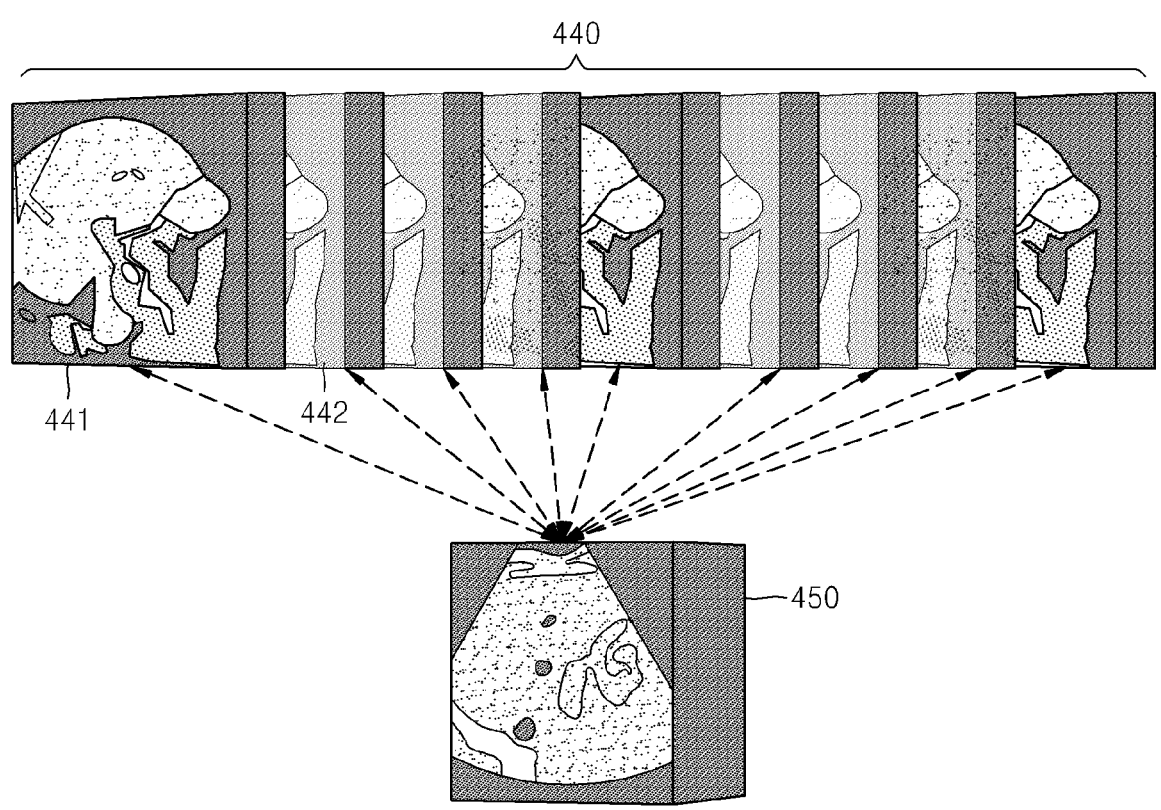
FIGS. 5, 6, and 7 illustrate additional registration, according to exemplary embodiments.

FIG. 5 illustrates a registration between all first medical images 440 belonging to a first medical image model and a second medical image 450. The first medical images 440 are images which are transformed based on a registration parameter which is determined based on a result of initial registration. As shown in FIG. 5, registration for all of the first medical images 440 is performed.

Figure 6:
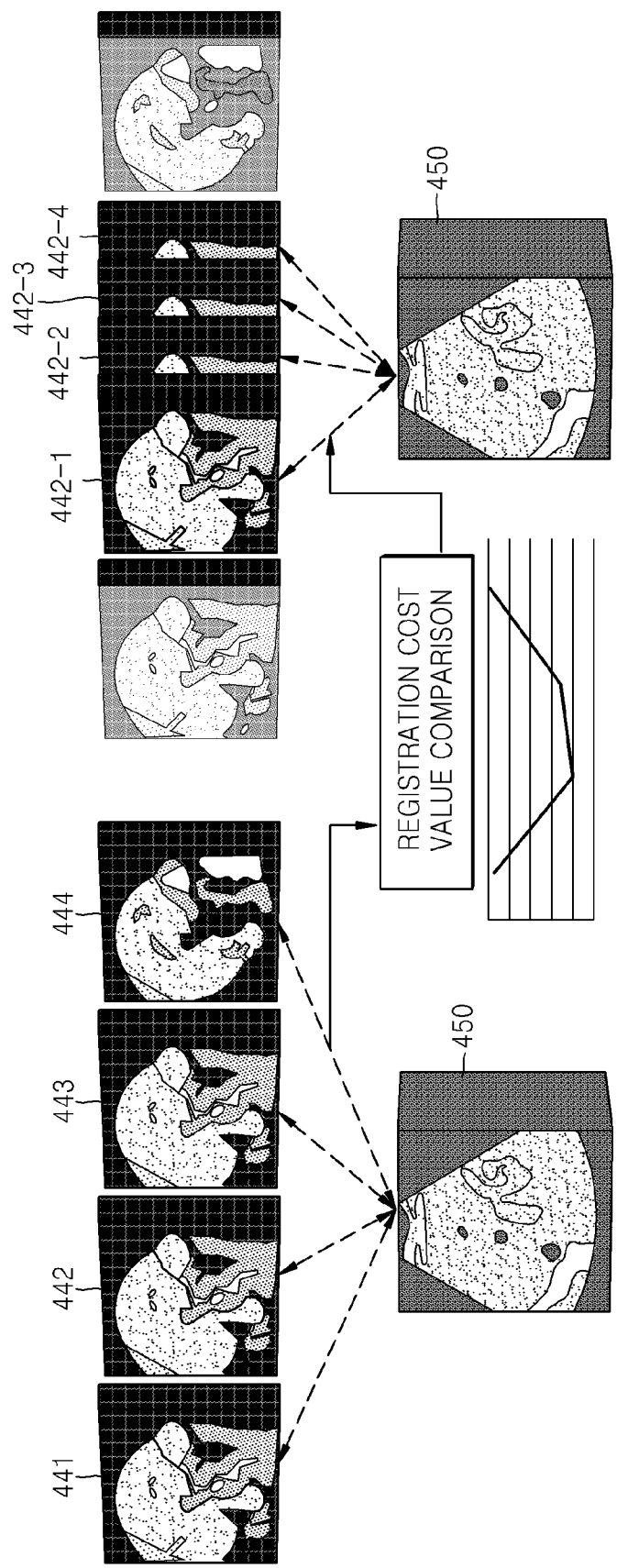

FIG. 6 illustrates an additional registration between three or four first medical images 441, 442, 443, and 444 and the second medical image 450. For example, the additional registration between each of the three or four first medical images 441, 442, 443, and 444 which are selected as corresponding to a near inhalation state, a half inhalation/exhalation state, and an exhalation state and one ultrasound image (the second medical image 450), and registration cost values thereof are compared with each other. Thereafter, the first medical image 442, for which the cost value is minimum, is determined, and a further additional registration is performed between interpolated first medical images 442-1, 442-2, 442-3, and 442-4 near the first medical image 442 and the second medical image 450.

Figure 7:
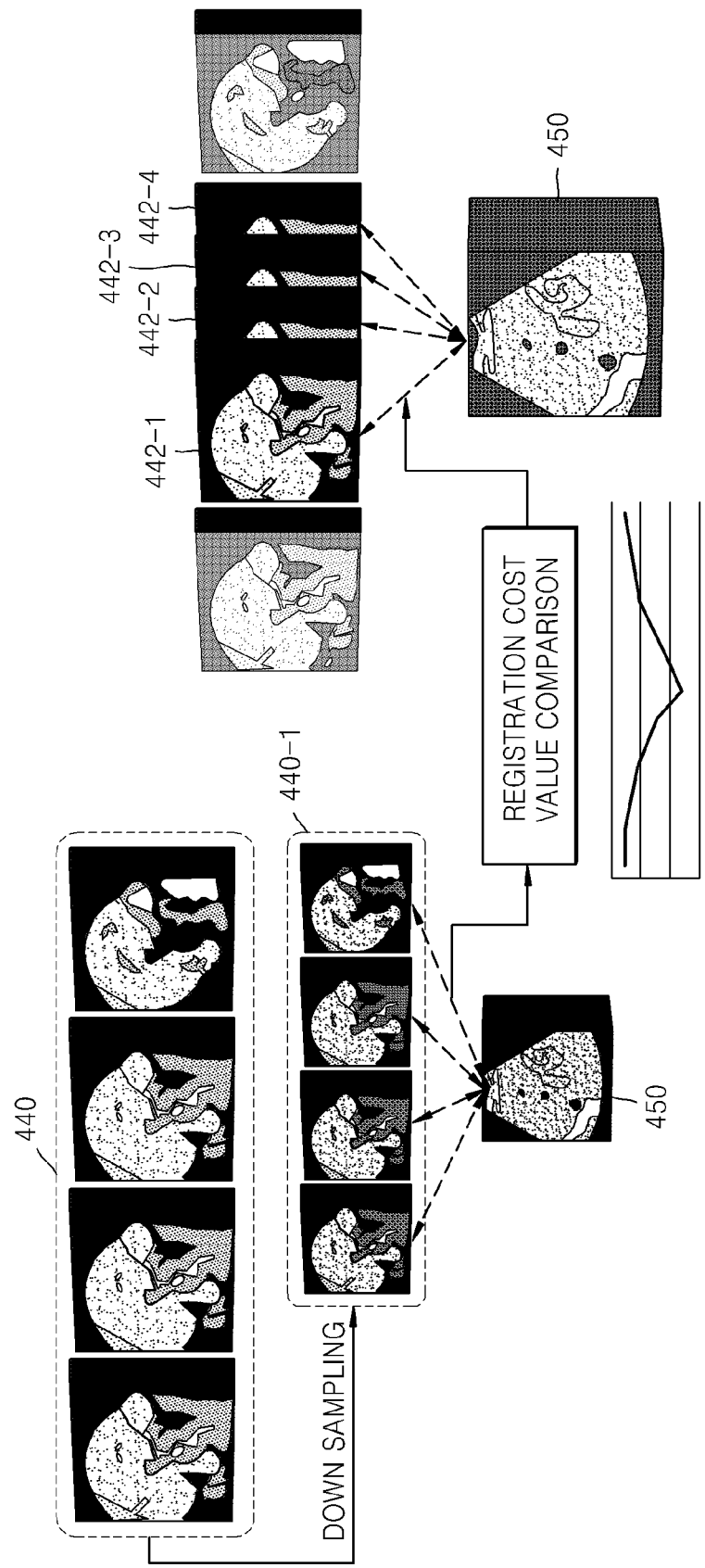

FIG. 7 illustrates a multi-resolution method which may be used when a speed of registration is relatively slow. First, first medical images 440 of a transformed first medical image model are down-sampled by approximately two or three levels, and an additional registration is performed between down-sampled first medical images 440-1 and the second medical image 450 by using a parallel processing method. Some images 442-1, 442-2, 442-3, and 442-4 near a first medical image 440-1 for which a registration cost value is minimum as a result of the additional registration are up-sampled, and an additional registration is performed again between the up-sampled images 442-1, 442-2, 442-3, and 442-4 and the second medical image 450.

The additional registration unit 240 may perform one or more additional registrations by applying any one or more of the three methods described above, and provide, to the medical image model generation unit 210, a first medical image for which a registration cost value is minimum, and/or first medical images for which registration cost values are relatively low. The medical image model generation unit 210 may update a previously generated first medical image model by interpolating the provided first medical image(s) by segmenting a displacement vector by a smaller interval than a previous displacement vector with respect to the provided first medical image(s). The additional registration unit 240 may perform addition additional registration(s) between the interpolated first medical image(s) and the second medical image.

The control unit 200 may control outputting of a first medical image matched with the second medical image by, for example, comparing cost values of the additional registration in the additional registration unit 240 with each other. When an additional registration is completed, the control unit 200 acquires a measurement value based on a respective intensity and a respective gradient of each of finally transformed first medical images, compares each measurement value with each other, and determines a first medical image having a maximum or minimum registration measurement value as an image most similar to a currently acquired second medical image. In particular, although only rigid registration has been performed in the initial registration and the additional registration in an intra-operative stage, a corresponding image may have high accuracy since the corresponding image is a registered image which includes even deformation information due to breathing. In addition, a highly accurate registration result in which deformation of a target organ due to breathing is also considered may be obtained by rigid registration which may be performed at a relatively fast speed. In addition, during a medical procedure, a registered image most similar to a currently acquired second medical image, e.g., a 3D ultrasound image, may be obtained even without performing non-rigid registration.

According to one or more exemplary embodiments, registration includes an operation in which coordinates used by the first medical device 110 and the second medical device 120 correspond to each other. A registered image may be a fusion image which is obtained by overlaying different medical images or an image which is obtained by arranging different medical images side by side. The medical image registered by the medical image registration apparatus 130 may be displayed by the image display device 140.

The medical image storage unit 250 stores the first medical image model generated by the medical image model generation unit 210, the first medical image captured by the medical image acquisition unit 220 before a medical procedure is conducted, the second medical image captured by the medical image acquisition unit 220 during the medical procedure, and the registered image.

FIG. 8 is a flowchart of a method for generating a non-real-time medical image model before a medical procedure is conducted.

Referring to FIGS. 3 and 8, in operation 800, the first medical images 300, 310, and 320 in two or more breathing states are acquired. The first medical images 300, 310, and 320 may be acquired by the first medical device 110 in a pre-operative stage in two or more breathing states of one breathing period t. In operation 802, non-rigid registration is performed between the first medical images 300, 310, and 320 of adjacent breathing states.

In operation 804, the interpolated first medical images 301, 302, 311, and 312 are acquired.

In operation 806, a first medical image model which includes the first medical images 300, 310, and 320 and the interpolated first medical images 301, 302, 311, and 312 is generated. The first medical images 300, 310, 320, and 301 may be 3D medical images, and the first medical image model may include 4D medical images.

A medical image registration method which is intended to be performed during a medical procedure will now be described with reference to FIGS. 4 and 9.

Figure 4:
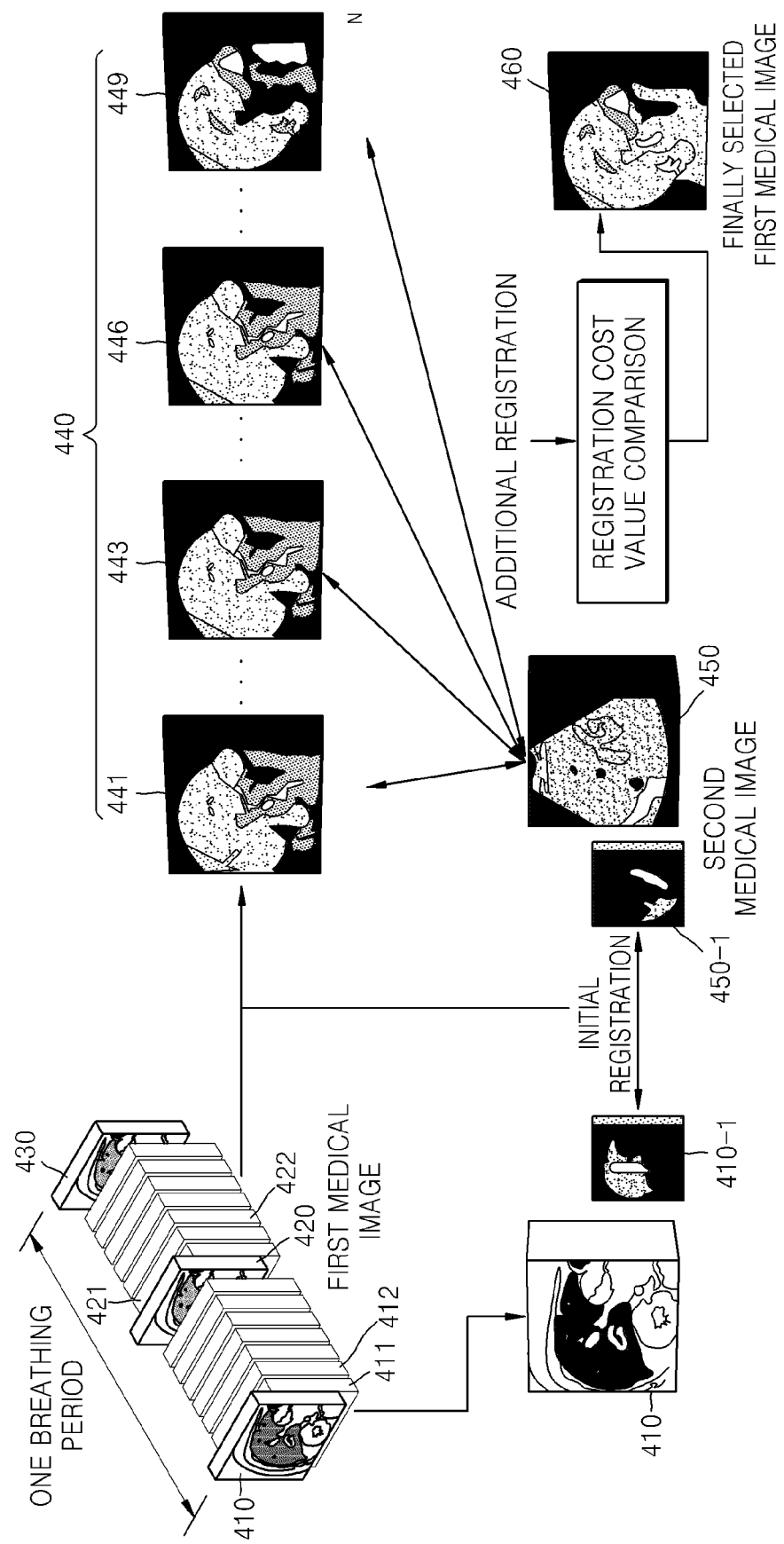
FIG. 4 illustrates a medical image registration method, according to an exemplary embodiment.

Referring to FIGS. 4 and 9, in operation 900, a second medical image 450 is acquired. In operation 902, an initial registration is performed between at least one first medical image 410 of a first medical image model and the second medical image 450. The initial registration may be a rigid registration based on a landmark point, and the initial registration is performed between a first medical image 410-1 and a second medical image 450-1 based on respective landmark points. A transformed first medical image model 440 is generated by transforming first medical images belonging to the first medical image model using a registration parameter which is determined based on a result of the initial registration. Although FIG. 4 illustrates the initial registration between the second medical image 450 and the one first medical image 410 as a reference image, the initial registration may be performed between the second medical image 450 and all first medical images, or between the second medical image 450 and three or four first medical images, as described above.

In operation 904, an additional registration is performed between at least one first medical image 441, 443, 446, or 449 of the transformed first medical image model 440 and the second medical image 450. The additional registration may include rigid matching based on an intensity and a gradient of each image. Various exemplary embodiments of the additional registration are the same as described with reference to FIGS. 5, 6, and 7.

In operation 906, registration cost values which are determined based on a result of the additional registration in operation 904 are compared with each other. In operation 908, a finally registered first medical image 460 is selected. The first medical image 460 which is finally registered with or most similar to the second medical image 450 is selected.

According to the medical image registration method and apparatus according to the one or more of the above-described exemplary embodiments, a highly accurate registration result in which deformation of a target organ due to breathing is also considered may be obtained by rigid registration which may be performed at a relatively fast speed. In addition, during a medical procedure, a registered image most similar to a currently acquired second medical image, e.g., a 3D ultrasound image, may be obtained even without performing non-rigid registration. In addition, a first medical image model in which breathing deformation information is considered, e.g., MR/CT images, may be generated in a pre-operative stage, and a highly accurate registered image in which the breathing deformation information is considered may be obtained by using additional registration during a medical procedure.

As described above, according to the one or more of the above-described exemplary embodiments, a highly accurate registered image in which breathing deformation information is considered may be obtained by generation of non-real-time medical images in which the breathing deformation information is reflected before a medical procedure is conducted and by rigid registration of a real-time medical image and the generated non-real-time medical images during the medical procedure.

An apparatus according to the exemplary embodiments may include a processor, a memory for storing and executing program data, a permanent storage such as a disk drive, a communication port for performing communication with an external device, and a user interface, such as a touch panel, a key, and a button. Methods implemented with a software module or an algorithm may be stored in a computer-readable recording medium in the form of computer-readable codes or program instructions executable in the processor. Examples of the computer-readable recording medium include magnetic storage media (e.g., read-only memory (ROM), random-access memory (RAM), floppy disks, hard disks, etc.) and optical recording media (e.g., CD-ROMs, Digital Versatile Discs (DVDs), etc.). The computer-readable recording medium can also be distributed over network coupled computer systems so that the computer-readable code is stored and executed in a distributed fashion. The media can be read by a computer, stored in the memory, and executed by the processor.

The exemplary embodiments can be represented with functional blocks and various processing steps. These functional blocks can be implemented by various numbers of hardware and/or software configurations for executing specific functions. For example, the exemplary embodiments may adopt direct circuit configurations, such as memory, processing, logic, and look-up table, for executing various functions under control of one or more processors or by other control devices. Like components being able to execute the various functions with software programming or software elements, the exemplary embodiments can be implemented by a programming or scripting language, such as C, C++, Java, or assembler, with various algorithms implemented by a combination of a data structure, processes, routines, and/or other programming components. Functional aspects can be implemented with algorithms executed in one or more processors. In addition, the exemplary embodiments may adopt the prior art for electronic environment setup, signal processing and/or data processing. The terms, such as "mechanism", "element", "means", and "configuration", can be widely used and are not delimited as mechanical and physical configurations. The terms may include the meaning of a series of routines of software in association with a processor.

Specific executions described in the exemplary embodiments are merely exemplary, and do not limit the scope of the present inventive concept even in any method. For conciseness of the specification, disclosure of conventional electronic configurations, control systems, software, and other functional aspects of the systems may be omitted. In addition, connections or connection members of lines between components shown in the drawings illustrate functional connections and/or physical or circuit connections, and the connections or connection members can be represented by replaceable or additional various functional connections, physical connections, or circuit connections in an actual apparatus.

The use of the term "said" or a similar directional term in the specification (in particular, in claims) may correspond to both the singular and the plural. In addition, when a range is disclosed in the present disclosure, inventions to which individual values belonging to the range are applied are included (if there is no disclosure opposed to this), and this is the same as if each of the individual values forming the range is disclosed in the detailed description. Finally, for steps forming the methods, if an order is not clearly disclosed or, if there is no disclosure opposed to the clear order, the steps can be performed in any order deemed proper. The exemplary embodiments are not necessarily limited to the disclosed order of the steps. The use of all illustrations or illustrative terms (for example, and so forth, etc.) in the exemplary embodiments is simply to describe the technical idea in detail, and the scope of the exemplary embodiments is not limited due to the illustrations or illustrative terms unless they are limited by claims. In addition, it will be understood by those of ordinary skill in the art that various modifications, combinations, and changes can be formed according to design conditions and factors within the scope of the attached claims or the equivalents.

In addition, other exemplary embodiments can also be implemented through computer-readable code/instructions in/on a medium, e.g., a transitory or non-transitory computer-readable medium, to control at least one processing element to implement any above-described exemplary embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer-readable code may be stored/transferred and executed in a distributed fashion. Furthermore, the processing element could include a processor or a computer processor, and processing elements may be distributed and/or included in a single device.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A medical image registration method comprising:
generating a first medical image set which includes a plurality of first medical images captured during at least two breathing states of an object and a plurality of interpolated medical images of intermediate breathing states that are adjacent to the at least two breathing states;
transmitting ultrasound signals to a region of interest (ROI) of the object and detecting reflected signals corresponding to the transmitted ultrasound signals;
acquiring a second medical image based on the reflected signals;
performing an initial registration, comprising a first rigid registration between at least a first one of the first medical images which is included in the generated first medical image set and the acquired second medical image;
transforming, by applying a transform function, the generated first medical image set by using a registration parameter which is determined based on the initial registration;
down-sampling a plurality of medical images which are included in the transformed first medical image set;
performing a second registration, comprising a second rigid registration, between the down-sampled plurality of medical images and the acquired second medical image;
determining, among the down-sampled plurality of medical images, a down-sampled medical image having a minimum registration cost value among registration cost values obtained by the second registration between the down-sampled plurality of medical images and the acquired second medical image;
updating the down-sampled plurality of medical images to include a plurality of additional interpolated medical images interpolated based on the determined down-sampled medical image;
up-sampling a subset of the updated down-sampled plurality of medical images, the subset including the determined down-sampled medical image;
performing an additional registration during an intraoperative stage, comprising a third rigid registration, between the up-sampled subset of the updated down-sampled plurality of medical images and the second medical image; and
displaying a combined image which is based on a result of the additional registration,
wherein the plurality of interpolated medical images is generated by a first interpolation using a displacement vector which is determined by performing a non-rigid registration with respect to the plurality of first medical images,
wherein the plurality of additional interpolated medical images is generated by a second interpolation using the displacement vector with respect to the determined down-sampled medical image, and
wherein an interval used for segmentation of the displacement vector in the second interpolation is smaller than in the first interpolation.

2. The medical image registration method of claim 1, wherein the plurality of interpolated medical images are interpolated by performing a linear segmentation or a non-linear segmentation of the displacement vector with respect to the plurality of first medical images.

3. The medical image registration method of claim 1, wherein the registration parameter is determined by matching respective landmark points of a first medical image captured during an inhalation state from among the at least two breathing states with corresponding landmark points of the second medical image, and wherein the transforming comprises transforming the first medical images included in the first medical image set by using the determined registration parameter.

4. The medical image registration method of claim 1, wherein at least three registration parameters are determined by matching respective landmark points of each of at least three from among the first medical images which respectively correspond to an inhalation state, a half inhalation/exhalation state, and an exhalation state from among the at least two breathing states with corresponding landmark points of the second medical image, and wherein an interpolated registration parameter is interpolated using the determined at least three registration parameters, and wherein the transforming comprises using the determined at least three registration parameters and the interpolated registration parameter.

5. The medical image registration method of claim 1, wherein a plurality of registration parameters are determined by matching respective landmark points of all of the first medical images with corresponding landmark points of the second medical image, and the transforming comprises using all of the plurality of registration parameters.

6. The medical image registration method of claim 1, wherein the second registration is performed based on an intensity and a gradient of a selected at least first one of the first medical images with respect to the second medical image.

7. The medical image registration method of claim 6, wherein the second registration is performed for at least three of the first medical images which correspond to an inhalation state, a half inhalation/exhalation state, and an exhalation state from among the at least two breathing states from the transformed first medical image set and the second medical image.

8. The medical image registration method of claim 1, wherein each of the first medical images includes one from among a magnetic resonance (MR) image, a computed tomography (CT) image, a positron emission tomography (PET) image, and an X-ray image captured before a medical procedure is conducted, and the second medical image includes one from among a 3D ultrasound image and a 2D ultrasound image captured during the medical procedure.

9. A medical image registration apparatus comprising:
a memory for executing program data;
an ultrasound probe configured to transmit ultrasound signals to a region of interest (ROI) of an object and detect reflected signals corresponding to the transmitted ultrasound signals; and
at least one processor configured to:
generate a first medical image set which includes a plurality of first medical images captured during at least two breathing states of a subject and a plurality of interpolated medical images of intermediate breathing states that are adjacent to the at least two breathing states;
acquire a second medical image based on the reflected signals;
perform an initial registration, comprising a first rigid registration, between at least a first one of the first medical images which is included in the generated first medical image set and the acquired second medical image;
transform, by applying a transform function, the first medical image set by using a registration parameter which is determined based on the initial registration;
down-sample a plurality of medical images which are included in the transformed first medical image set;
perform a second registration, comprising a second rigid registration, between the down-sampled plurality of medical images and the acquired second medical image;
determine, among the down-sampled plurality of medical images, a down-sampled medical image having a minimum registration cost value among registration cost values obtained by the second registration between the down-sampled plurality of medical images and the acquired second medical image;
update the down-sampled plurality of medical images to include a plurality of additional interpolated medical images interpolated based on the determined down-sampled medical image;
up-sample a subset of the updated down-sampled plurality of medical images, the subset including the determined down-sampled medical image;
perform an additional registration during an intraoperative stage, comprising a third rigid registration, between the up-sampled subset of the updated down-sampled plurality of medical images and the second medical image; and
display a combined image which is based on a result of the additional registration,
wherein the plurality of interpolated medical images is generated by a first interpolation using a displacement vector which is determined by performing a non-rigid registration with respect to the plurality of first medical images,
wherein the plurality of additional interpolated medical images is generated by a second interpolation using the displacement vector with respect to the determined down-sampled medical image, and
wherein an interval used for segmentation of the displacement vector in the second interpolation is smaller than in the first interpolation.

10. The medical image registration apparatus of claim 9, wherein the plurality of interpolated medical images are interpolated by performing a linear segmentation or a non-linear segmentation of the displacement vector with respect to the plurality of first medical images.

11. The medical image registration apparatus of claim 9, wherein the at least one processor is further configured to perform the second registration based on an intensity and a gradient of the at least first one of the first medical images and the second medical image.

12. The medical image registration apparatus of claim 9, wherein each of the first medical images includes one from among a magnetic resonance (MR) image, a computed tomography (CT) image, a positron emission tomography (PET) image, and an X-ray image captured before a medical procedure is conducted, and the second medical image includes one from among a 3D ultrasound image and a 2D ultrasound image captured during the medical procedure.

* * * * *